United States Patent [19]

Badorc et al.

[11] Patent Number: 4,847,265

[45] Date of Patent: Jul. 11, 1989

[54] DEXTRO-ROTATORY ENANTIOMER OF METHYL ALPHA-5 (4,5,6,7-TETRAHYDRO (3,2-C) THIENO PYRIDYL) (2-CHLOROPHENYL)-ACETATE AND THE PHARMACEUTICAL COMPOSITIONS CONTAINING IT

[75] Inventors: Alain Badorc, Roquettes; Daniel Fréhel, Toulouse, both of France

[73] Assignee: Sanofi, France

[21] Appl. No.: 155,550

[22] Filed: Feb. 12, 1988

[30] Foreign Application Priority Data

Feb. 17, 1987 [FR] France ................................ 87 02025
Nov. 27, 1987 [FR] France ................................ 87 16516

[51] Int. Cl.$^4$ ..................... A61K 31/44; C07D 495/04
[52] U.S. Cl. ..................................... 514/301; 546/114
[58] Field of Search ......................... 546/114; 514/301

[56] References Cited

U.S. PATENT DOCUMENTS 4,529,596 7/1985 Aubert et al. ...................... 546/115

FOREIGN PATENT DOCUMENTS 0099802 7/1983 European Pat. Off. .

OTHER PUBLICATIONS

Fieser et al., Advanced Org. Chem.-Reinhold Publishing Co., N.Y., (1961), pp. 85–88.

*Primary Examiner*—Mary C. Lee
*Assistant Examiner*—Bernard I. Dentz
*Attorney, Agent, or Firm*—Wegner & Bretschneider

[57] ABSTRACT

The present invention relates to the dextro-rotatory enantiomer of Formula

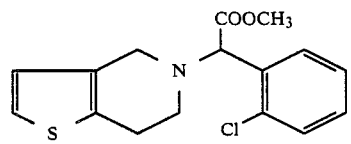

and its pharmaceutically acceptable salts with platelet aggregation inhibiting activity.

The invention also relates to a process for the preparation of this compound starting from the racemate and the pharmaceutical compositions containing it.

7 Claims, No Drawings

DEXTRO-ROTATORY ENANTIOMER OF METHYL ALPHA-5 (4,5,6,7-TETRAHYDRO (3,2-C) THIENO PYRIDYL) (2-CHLOROPHENYL)-ACETATE AND THE PHARMACEUTICAL COMPOSITIONS CONTAINING IT

The present invention relates to the dextro-rotatory enantiomer of methyl alpha-5(4,5,6,7-tetrahydro(3,2-c)thieno pyridyl) (2-chlorophenyl)-acetate, a process for its preparation and pharmaceutical compositions containing it.

The compound of the invention corresponds to the following formula (I):

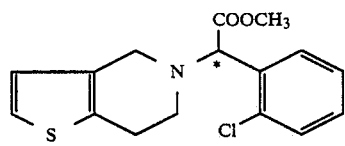

in which the C* is an asymmetric carbon atom. In fact, this formula represents both the dextro-rotatory molecule claimed as well as its levo-rotatory enantiomer. The racemic mixture corresponding to this formula was described in the French patent application published under the No. 2 530 247. Hereafter the dextro-rotatory enantiomer claimed according to the invention will be designated by $I_d$ and the levo-rotatory enantiomer by $I_l$.

It is known that the optical rotatory power of a compound depends on the solvent in which it is measured and on its concentration in this solvent. The optical rotatory power of the dextro-rotatory isomer according to the invention is positive in methanolic solution.

In an unexpected manner only the dextro-rotatory enantiomer $I_d$ exhibits a platelet aggregation inhibiting activity, the levo-rotatory enantiomer $I_l$ being inactive. Moreover, the inactive levo-rotatory enantiomer $I_l$ is the less well tolerated of the two enantiomers.

The invention also relates to the addition salts of the compounds of formula ($I_d$) with pharmaceutically acceptable mineral or organic acids.

The compound ($I_d$) is an oil whereas its hydrochloride exists as a white powder. The oily products are usually difficult to purify and it is preferable to use for the preparation of pharmaceutical compositions crystalline products which can usually be purified by recrystallization.

However, it has been observed in the present case that some of the salts of compound ($I_d$) usually precipitate in an amorphous form and/or that they are hygroscopic, a property which makes them difficult to handle on an industrial scale. Thus, the salts of carboxylic acid and sulfonic acids classically used in pharmacy have been prepared, acids such as acetic, benzoic, fumaric, maleic, citric, tartaric, gentisic, methane-sulfonic, ethanesulfonic, benzenesulfonic and laurylsulfonic acids as well as the salts of dobesilic acid (m.p.=70° C.) and para-toluenesulfonic acid (m.p.=51° C.), the purification of which proved to be difficult.

Among the mineral and organic acid salts of the dextro-rotatory isomer of the compound of Formula ($I_d$) salts have been found which crystallize easily, are not hygroscopic and are sufficiently water-soluble as to make their use as active medicinal principles particularly advantageous.

The present invention thus relates more particularly to the hydrogen sulfate, the taurocholate and the hydrobromide of the dextro-rotatory enantiomer of methyl alpha-5(4,5,6,7-tetrahydro(3,2-c)thieno pyridyl) (2-chlorophenyl)-acetate.

These salts are prepared in a standard manner by the action of the corresponding acid on the base in solution in a solvent from which they precipitate spontaneously or after addition of a non-solvent of the salt.

The dextro-rotatory isomer of methyl alpha-5(4,5,6,7-tetrahydro(3,2-c)thieno pyridyl) (2-chlorophenyl)-acetate can be prepared by forming the salt of the racemic compound with an optically active acid in a solvent, repeated recrystallizations of the salt until a product of constant optical rotatory power is obtained, followed by the liberation of the dextro-rotatory isomer from its salts by a base; if required, a salt is formed between the dextro-rotatory isomer and a pharmaceutically acceptable acid.

The optically active acid may advantageously be levo-rotatory camphor-10-sulfonic acid.

One and the same solvent may be used for salt formation and recrystallization: acetone is ideally suited in this case.

The chiral, levo-rotatory camphor-10-sulfonic acid of Formula ($II_l$) is allowed to react in an inert solvent with the racemic mixture of Formula (I) according to the following reaction scheme:

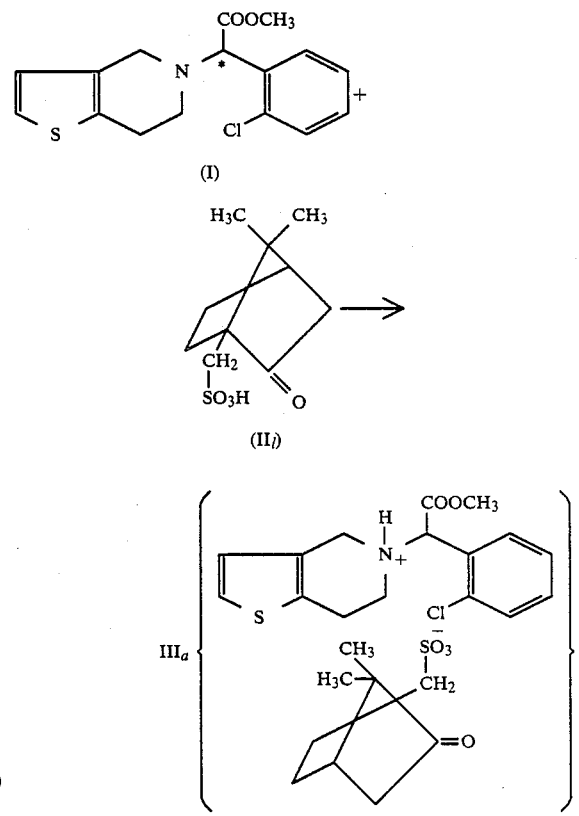

Salt formation may be carried out in solvents such as alcohols, ketones, dimethylformamide. The salt precipitates spontaneously or is isolated by salting out or evaporation of the solvent. A mixture of two diastereoisomers of Formula (IIIa) is formed. By repeated recrystallizations from a solvent such as acetone the precipitate is enriched in the salt of the dextro-rotatory isomer of compound (I). After each recrystallization the optical rotatory power $[\alpha]_D^{20}$ of the precipitate is measured at 20° C. in methanol at a concentration varying between 1.5 and 2 g/100 ml. When the $[\alpha]_D^{20}$ stops increasing the base of Formula ($I_D$) is liberated from the salt (IIIa) by the action of a base such as sodium or potassium hydrogen carbonate in aqueous media at temperatures varying between 5° C. and 20° C. Evaporation of the filtrate of the first recrystallization IV after the crystals of the precipitated salt (IIIa) have been filtered off, gives a mixture enriched in the salt of ($I_l$) enantiomer. The basification of this mixture of diastereoisomeric salts with a weak base such as sodium or potassium hydrogen carbonate in aqueous solution at temperatures varying between 5° C. and 20° C. leads to a mixture of the two enantiomers ($I_d$) plus ($I_l$) enriched in the levo-rotatory enantiomer ($I_l$).

This mixture ($I_d$)+($I_l$) enriched in enantiomer ($I_l$) is allowed to react with dextro-rotatory camphor-10-sulfonic acid which will be designated as ($II_d$) in a solvent according to the following reaction scheme:

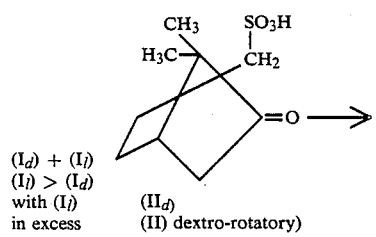

($I_d$) + ($I_l$)
($I_l$) > ($I_d$)
with ($I_l$)    ($II_d$)
in excess    (II) dextro-rotatory)

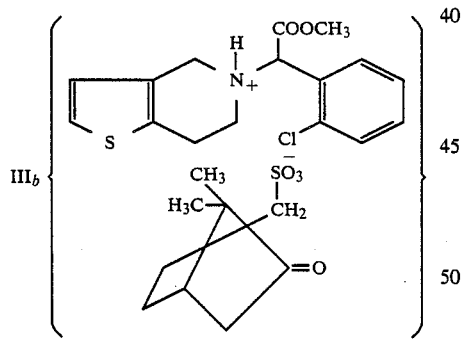

III$_b$

The crystalline mixture of diastereoisomeric salts (IIIb) obtained is recrystallized from acetone until the optical rotatory power $[\alpha]_D^{20}$ of the precipitate remains constant. As previously mentioned the optical rotatory power $[\alpha]_D^{20}$ of the diastereoisomeric salt (IIIb) is determined after each recrystallization.

The liberation of the stereoisomeric ($I_l$) from its salt is carried out in a standard manner, like that for compound ($I_d$). Levo-rotatory comphor-10-sulfonic acid ($II_l$) may be obtained from commercially available ammonium camphor-10-sulfonate of Formula (V) according to the reaction scheme:

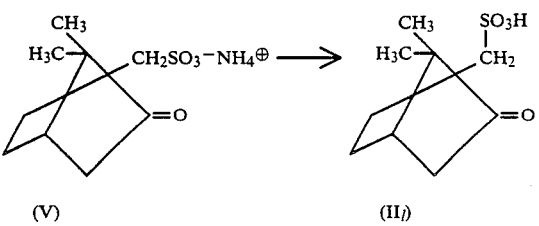

An aqueous solution of the ammonium salt (V) is chromatographed on an Amberlite IRN-77 resin. After lyophilization of the eluate camphor-10-sulfonic acid of Formula ($II_l$) is recovered.

The entire sequence of the process is shown schematically below:

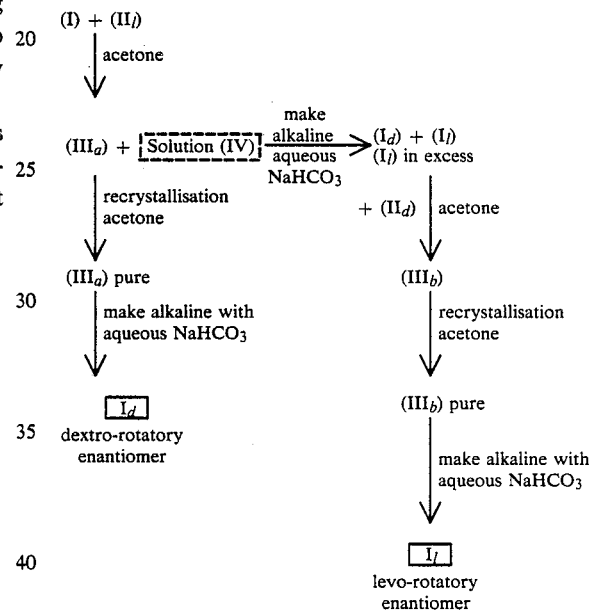

Each of the pure enantiomers ($I_d$) and ($I_l$) may be converted into a salt by means of the standard methods: for example, the hydrochlorides are prepared by the addition of a solution of hydrogen chloride gas in diethyl ether to a solution of ($I_d$) or ($I_l$) in diethyl ether.

DETERMINATION OF THE ENANTIOMERIC PURITY OF THE DEXTRO-ROTATORY ($I_d$) AND LEVO-ROTATORY ($I_l$) ENANTIOMERS

Two methods have been used:
proton NMR spectroscopy with the addition of a chiral rare earth
high pressure liquid chromatography using a chiral stationary phase.

(a) Proton NMR spectroscopy with the addition of a chiral rare earth The enantiomeric purity (optical purity) was determined by $^1$H 60 MHz NMR spectroscopy in the presence of a rare earth chiral complex according to the method described by G. M. WHITESIDES et al. (J. Am. Chem. Soc. 1974, 96, 1038).

In the racemic product (I), the hydrogen attached to the asymmetric centre in the α position to the ester function appears as a singlet (chemical shift δ=4.87 ppm in CDCl$_3$ as solvent. The addition of the rare earth complex Eu(tfc)$_3$ [tris 3-(trifluoromethyl hydroxymethylene)-d-camphorato europium (III)] to the probe containing a solution of the racemate (I) in CDCl$_3$ leads to the resolution of the initial singlet into two, well-separated singlets corresponding to the proton of each of the two enantiomers (I$_d$) and (I$_1$). When the molar ratio of rare earth complex/compound (I)=0.4, the separation between the two singlets is about 6 Hz.

With each of the two enantiomers prepared, (I$_d$) and (I$_1$), the same procedure was used as for the racemate (I). The smaller chemical shift corresponds to the proton of the dextro-rotatory enantiomer (I$_d$) and the larger chemical shift to the levo-rotatory enantiomer (I$_1$).

The precision of the method was determined by comparing the $^1$H (60 MHz) NMR spectra obtained with and without addition of the rare earth complex for each of the two enantiomers (I$_d$) and (I$_1$) in the pure state or as mixtures containing increasing quantities of one of the enantiomers. It was observed that it was possible to detect easily more than 5% by weight of one enantiomer in the presence of the other.

(b) High pressure liquid chromatography using a chiral stationary phase The study was conducted with a liquid chromatograph HP-1084 using a UV detector at 215 nm. The chiral stationary phase was DEAE silica (10 microns) onto which was grafted alpha-1 acid glycoprotein (0.4×100 mm) (ENANTIOPAC R-LKB). The mobile phase consisted of an aqueous phosphate buffer mixture 8 mM (NaH$_2$PO$_4$/Na$_2$HPO$_4$) containing 0.1M of NaCl, adjusted to pH=7.4, and 15% of isopropanol (v/v). The flow rate was fixed at 0.3 ml/minute and the temperature of the column was maintained at 18°–20° C. Under these conditions, the dextro-rotatory enantiomer (I$_d$) has a retention time of 45 minutes and the levo-rotatory enantiomer (I$_1$) has a retention time of 35 minutes.

The precision of the determination of the optical purity of the two enantiomers was estimated by chromatographing each of the two enantiomers (I$_d$) and (I$_1$) prepared either alone or as a mixture containing increasing amounts of one of the enantiomers. It was observed that it was easy to detect:

2% (weight/weight) of enantiomer (I$_d$) in enantiomer (I$_1$)

4% (weight/weight) of enantiomer (I$_1$) in enantiomer (I$_d$).

Under these conditions it may be concluded that the optical purity of the two enantiomers (I$_d$) and (I$_1$) obtained according to the examples is at least equal to 96% for the dextro-rotatory enantiomer (I$_d$) and at least equal to 98% for the levo-rotatory enantiomer (I$_1$).

The following examples are non-restrictive and are presented to illustrate the present invention.

EXAMPLE 1

Salts of dextro-rotary methyl-alpha-5(4,5,6,7-tetrahydro(3,2-c)thieno pyridyl) (2-chlorophenyl)-acetate (a) levo-rotatory camphor-10-sulfonic acid A column of Amberlite IRN-77 resin is prepared and tested by passing 1N hydrochloric acid through it and then by washing this column of acidified resin abundantly with water. Levo-rotatory ammonium camphor-10-sulfonate is dissolved in a minimum of water and applied to the column of resin previously prepared. Elution is carried out with water. The eluted fractions containing the acid are lyophilized.

White crystals, m.p.=198° C.; [α]$_D^{20}$=−20.53 (c=2.075 g/100 ml water).

(b) Camphor-10-sulfonic acid salt of methyl alpha-5(4,5,6,7-tetrahydro(3,2-c)thieno pyridyl) (2-chlorophenyl)-acetate (SR 25990 B).

32 g (0.0994 mole) of racemic methyl alpha-5(4,5,6,7-tetrahydro(3,2-c)thieno pyridyl) (2-chlorophenyl)-acetate are dissolved in 150 ml of acetone. 9.95 g (0.0397 mole) of levo-rotat camphor-10-sulfonic acid monohydrate are added. The clear solution is left to stand at room temperature. After 48 hours some crystals have formed. The reaction mixture is concentrated to 50 ml and left to stand at room temperature for 24 hours. The crystals obtained are filtered off, washed with acetone and dried (yield: 55% on the basis of the starting racemate).

White crystals, m.p.=165° C., [α]$_D^{20}$=+24.67 (c=1.58 g/100 ml; methanol).

The crystals obtained above are redissolved in the minimum of boiling acetone (50 ml). The crystals obtained after cooling are filtered off, washed with acetone and dried (yield: 88%).

White crystals, m.p.=165° C., [α]$_D^{20}$=+24.75 (c=1.68 g/100 ml; methanol).

(c) Dextro-rotatory methyl alpha-5(4,5,6,7-tetrahydro(3,2-c)thieno pyridyl) (2-chlorophenyl)-acetate.

12 g (0.022 mole) of the pure product obtained in (b) are dissolved in a minimum of water. After cooling to 5° C., the aqueous solution obtained is made alkaline with a saturated aqueous solution of sodium hydrogen carbonate. The alkaline aqueous phase is extracted with dichloromethane. The organic extracts are dried over anhydrous sodium sulfate. On evaporation of the solvent a colorless oil is obtained (quantitative yield). Oil, [α]$_D^{20}$=+51.52 (c=1.61 g/100 ml; methanol).

(d) The hydrochloride of methyl alpha-5(4,5,6,7-tetrahydro(3,2-c)thieno pyridyl) (2-chlorophenyl)-acetate (dextro-rotatory) (SR 25990 A).

7 g (0.0228 mole) of dextro-rotatory methyl alpha-5(4,5,6,7-tetrahydro(3,2-c)thieno pyridyl) (2-chlorophenyl)-acetate are dissolved in 100 ml of diethyl ether. 30 ml of a solution of 1N HCl in diethyl ether are added and the crystals obtained are filtered off. The crystals are washed with diethyl ether and dried (yield: 94%).

White crystals, m.p.=117° C., [α]$_D^{20}$=+62.23 (c=1.82 g/100 ml; methanol).

(e) The hydrogen sulfate of dextro-rotatory methyl alpha-5(4,5,6,7-tetrahydro(3,2-c)thieno pyridyl) (2-chlorophenyl)-acetate (SR 25990 C).

800 ml of a saturated aqueous solution of sodium bicarbonate are added to a suspension of 200 g of SR 25990 B in 800 ml of dichloromethane. After vigorous shaking, the organic phase is separated, dried over sodium sulfate and the solvent is removed under reduced pressure. The residue is dissolved in 500 ml of ice-cold acetone and 20.7 ml of concentrated sulfuric acid (93.64%, d=1.83) are added drop-wise. The precipitate formed is isolated by filtration and washed with 1,000 ml of acetone, then dried in a vacuum oven at 50° C.

139 grams of analytically pure white crystals are thus obtained with a melting point of 184° C. Empirical formula: C$_{16}$H$_{16}$ClNO$_2$S.H$_2$SO$_4$ [α]$_D^{20}$=+55.10 (c=1.891 g/100 ml; methanol).

(f) The hydrobromide of dextro-rotatory methyl alpha-5(4,5,6,7-tetrahydro(3,2-c)thieno pyridyl) (2-chlorophenyl)-acetate (SR 25990D).

150 ml of an aqueous solution of sodium bicarbonate are added to a suspension of 20 g of SR 25990 B in 200 ml of dichloromethane. The residue obtained after separation of the organic phase, drying and evaporation of the solvent is dissolved in 150 ml of diethyl or diisopropyl ether, and 4.4 ml of a 48% (wt/v) aqueous solution of hydrobromic acid are added drop-wise. The precipitate formed is isolated. After drying, 14.4 g of crystals are obtained with a melting point of 111° C. (yield 99%).

13.4 g of these crystals are recrystallized from a mixture of isopropyl ether (100 ml) and isopropanol (150 ml) to give 10.2 g of analytically pure hydrobromide: m.p.=140° C.; empirical formula: $C_{16}H_{16}ClNO_2S.HBr$ $[\alpha]_D^{20}=+59.23$ (c=2.09 g/100 ml; methanol).

(g) The taurocholate of dextro-rotatory methyl alpha-5(4,5,6,7-tetrahydro(3,2-c)thieno pyridyl) (2-chlorophenyl)-acetate (SR 25990E).

The sodium salt of taurocholic acid is chromatographed on Amberlite IRN-77 resin by eluting with water. The fractions obtained are lyophilized.

3 g (0.0054 mole) of SR 25990B are treated with a saturated aqueous solution of sodium bicarbonate and the mixture is extracted with dichloromethane. The organic phase is separated, dried over sodium sulfate and evaporated to dryness. The free base obtained is taken up in 30 ml of isopropanol; 2.8 g (0.0054 mole) of taurocholic acid dissolved in 100 ml of isopropanol are added to this solution. The mixture is stirred overnight at room temperature, then evaporated to dryness. The residue solidifed on being triturated with ether. 3.5 g of beige crystals are obtained. m.p.=120° C. $[\alpha]_D^{20}+=39.53$ (c=1.791 g/100 ml of methanol). $C_{16}H_{16}ClNO_2S.C_{26}H_{45}NO_7S$; C, H, N analyses in agreement with theory.

EXAMPLE 2

Salts of levo-rotatory methyl alpha-5(4,5,6,7-tetrahydro(3,2-c)thieno pyridyl) (2-chlorophenyl)-acetate (a) Salt of d-camphor-10-sulfonic acid (SR 25989 B)

After separation of SR 25990 B in Example 1-b the solvent is evaporated from the acetone filtrate obtained.

The residue is taken up in water and diethyl ether. The ethereal phase is decanted. The aqueous phase is cooled to 5° C. and made alkaline with a saturated aqueous solution of sodium bicarbonate. The aqueous alkaline phase is extracted with diethyl ether. The ethereal extracts are pooled and dried over anhydrous sodium sulfate.

On evaporation of the solvent an oil is obtained which is purified by filtration through a bed of silica (eluant: diethyl ether). A colourless oil is recovered consisting of a mixture of about 65% of the levo-rotatory enantiomer and 35% of the dextro-rotatory enantiomer, proportions determined by means of $^1H$ (60 MHz) NMR spectroscopy after the addition of chiral, rare earth complex.

16.66 g (0.0517 mole) of the mixture thus obtained are dissolved in 70 ml of acetone. 7.77 g (0.0310 mole) of dextro-rotatory camphor-10-sulfonic acid monohydrate are added. The homogeneous mixture is left to stand overnight at room temperature. The crystals obtained are filtered off, washed with acetone and dried (yield: 44% based on the mixture).

The crystals obtained are dissolved in a minimum of refluxing acetone (60 ml). The precipitate obtained on cooling to room temperature is filtered off, washed with acetone and dried. White crystals, m.p.=167° C., $[\alpha]_D^{20}=-24.85$ (c=1.79 g/100 ml; methanol).

(b) Levo-rotatory methyl alpha-5(4,5,6,7-tetrahydro(3,2-c)thieno pyridyl) (2-chlorophenyl)-acetate.

11.3 g (0.0204 mole) of the camphor-10-sulfonate obtained in (a) are dissolved in a minimum of water. The aqueous solution obtained is cooled to 5° C. and made alkaline with a saturated aqueous solution of sodium hydrogen carbonate. The alkaline aqueous phase is extracted with dichloromethane. The organic solution is dried and the solvent is evaporated. A colourless oil is isolated (quantitative yield).

Oil $[\alpha]_D^{20}=-50.74$ (c=1.58 g/100 ml; methanol).

(c) The hydrochloride of levo-rotatory methyl alpha-5(4,5,6,7-tetrahydro(3,2-c)thieno pyridyl) (2-chlorophenyl)-acetate (SR 25989 A).

Prepared according to the method described in Example 1(d). Yield: 94%.

White crystals, m.p.=117° C., $[\alpha]_D^{20}=-62.56$ (c=1.80 g/100 ml; methanol).

(d) The hydrogen sulfate of levo-rotatory methyl-alpha-5(4,5,6,7-tetrahydro(3,2-c)thieno pyridyl) (2-chlorophenyl)-acetate (SR 25989 C).

70 g (0.126 mole) of the camphor sulfonate SR 25989 B obtained are treated as described in (a) above with a saturated aqueous solution of sodium bicarbonate in the presence of dichloromethane. The organic phase is separated, dried over sodium sulfate and evaporated to dryness. The residue is taken up in 300 ml of acetone and 7.2 ml (0.126 mole) of concentrated sulfuric acid are added drop-wise. After being stirred the crystals formed are filtered off and washed with acetone. 47.8 g of white crystals are obtained. m.p.=182° C. $[\alpha]_D^{20}=-51.61$ (c=2.044 g/100 ml; methanol). The analysis (C,H,N) are in agreement with theory.

PHARMACOLOGICAL STUDY

The platelet aggregation inhibiting activity and the toxicity of these new compounds were compared to those of the racemic mixture described in the French Pat. No. 82.12599 (Publication No. 2 530 247).

A description will now be given of the results of this study which demonstrates another advantage of the invention, namely that the salts of the dextro-rotatory isomer have a better therapeutic index than the salt of the racemic mixture; in fact, the levo-rotatory isomer exhibits almost no platelet aggregation inhibiting activity and its toxicity is markedly higher than that of its dextro-rotatory homologue.

The platelet aggregation inhibiting activities and the antithrombotic activities of the compounds were studied in the rat by standard methods.

The activity on the aggregation of plates induced by ADP or collagen was determined ex-vivo.

The products dissolved in ethanol (200 mg/ml) and diluted in water containing gum arabic (5%-wt/v) were administered by the oral route to groups of five female rats of the CD-COBS strain, weighing 250–300 g, in amounts of 10 ml of suspension per kilogram two hours before blood samples were taken.

The blood samples were taken from animals anesthetized with diethyl ether by puncture of the abdominal aorta and placed over a 3.8% aqueous solution of sodium citrate (1 vol/9 volumes of blood). The platelet-rich plasma was then isolated by centrifugation at 200 g for 10 minutes.

Aggregation is induced by the addition of 2 μl of aggregating solution to 400 μl of platelet-rich plasma.

The aggregating solutions used were: a 500 μM aqueous solution of ADP marketed by Boehringer Mannheim (final concentration 2.5 μM), and a solution of collagen marketed by Sigma (type 1) at a concentration of 0.25 g/100 ml in 3% acetic acid (v/v) (final concentration 12.5 μg/ml).

The aggregation of the platelets was monitored as described in the method by G. V. R. Born in Nature 194, p. 927 (1967) using a Coultronics ® aggregometer at a temperature of 37° C. and agitation of 900 rpm.

For aggregation with ADP, the aggregometer generates a curve representing a platelet aggregation as measured by a change in optical density. The height of this curve is defined as the height of aggregation. The percentage of aggregation is the relation between the aggregation height measured and the height corresponding to 100% aggregation × 100. The percentage of inhibition is determined by the relation:

$$\frac{\text{Control aggregation height} - \text{produced aggregation height}}{\text{Control aggregation height}} \times 100$$

The results obtained for the aggregation with ADP for the hydrochloride of the racemic mixture (PCR 4099), the hydrogen sulfates of the dextro-rotatory (SR 25990 C) and levo-rotatory (SR 25989 C) isomers on the one hand, and for PCR 4099 and the hydrochlorides of the dextro-rotatory (SR 25990 A) and levo-rotatory (SR 25989 A) on the other, are shown in Table I; they demonstrate that the levo-rotatory isomer is inactive and that the dextro-rotatory isomer is at least as active as the racemate.

TABLE I

| PRODUCT | DOSE mg/Kg P.O | QUANTITY of base administered | % INHIBITION | P** |
|---|---|---|---|---|
| | | % AGGREGATION | | |
| Controls | | 42.4 +/− 1.5 | | |
| PCR 4099 | 4.48 | 3.84 | 29.8 +/− 2.4 | 30 | 0.01 |
| (racemate) | 8.97 | 7.69 | 17.2 +/− 2.2 | 59 | 0.001 |
| | 17.9 | 15.38 | 11.1 +/− 2.3 | 74 | 0.001 |
| SR 25989C | 20 | 15.38 | 41.0 +/− 1.5 | 3 | n.s |
| | 40 | 30.76 | 37.1 +/− 1.7 | 13 | n.s |
| SR 25990C | 1.25 | 0.96 | 39.4 +/− 1.3 | 7 | n.s |
| | 2.5 | 1.92 | 28.4 +/− 2.3 | 33 | 0.01 |
| | 5 | 3.84 | 14.0 +/− 1.6 | 67 | 0.001 |
| | 10 | 7.69 | 8.5 +/− 1.6 | 80 | 0.001 |
| Controls | | 33.8 +/− 2.3 | | |
| SR 25990E | 10 | 3.84 | 9.6 +/− 3 | 72 | 0.001 |
| | 20 | 7.69 | 4 +/− 1.6 | 88 | 0.001 |
| | | AGGREGATION HEIGHT | | |
| Controls | | 103 +/− 5 | | |
| PCR 4099 | 2.5 | 2.14 | 86 +/− 5 | 17 | 0.05 |
| (racemate) | 5 | 4.28 | 72 +/− 8 | 30 | 0.05 |
| | 12.5 | 10.71 | 32 +/− 9 | 69 | 0.001 |
| SR 25989A | 25 | 22.46 | 101 +/− 1 | 2 | n.s |
| SR 25990A | 2.5 | 2.25 | 67 +/− 7 | 35 | 0.01 |
| | 5 | 4.49 | 26 +/− 5 | 75 | 0.001 |
| | 12.5 | 11.23 | 19 +/− 4 | 82 | 0.001 |
| | 25 | 22.46 | 11 +/− 1 | 89 | 0.001 |

*mean of results +/− standard error of the mean (SEM)
**Student test
***aggregation height in mm: mean +/− SEM (n = 5)
n.s. not significant For the aggregation with collagen, the percentage of inhibition is the difference of the slopes of the curves representing the variation of the optical density as a function of time for the control and the product to be tested divided by the slope of the control multiplied by 100. The results shown in Table II demonstrate again that only the dextro-rotatory isomer is active whereas the salts have comparable activities.

TABLE II

| PRODUCT | DOSE mg/Kg P.O | QUANTITY of base administered | SLOPE | % INHIBITION | P** |
|---|---|---|---|---|---|
| Controls | | | 4.8 +/− 0.3 | | |
| PCR 4099 | 4.48 | 3.84 | 3.6 +/− 0.2 | 25 | 0.05 |
| (racemate) | 8.97 | 7.69 | 2.7 +/− 0.3 | 44 | 0.01 |
| | 17.9 | 15.38 | 1.5 +/− 0.3 | 69 | 0.001 |
| SR 25989C | 20 | 15.38 | 4.3 +/− 0.2 | 10 | n.s |
| | 40 | 30.76 | 4.0 +/− 0.2 | 17 | n.s |
| SR 25990C | 1.25 | 0.96 | 4.5 +/− 0.3 | 6 | n.s |
| | 2.5 | 1.92 | 4.1 +/− 0.2 | 15 | n.s |
| | 5 | 3.84 | 2.3 +/− 0.1 | 52 | 0.001 |
| | 10 | 7.69 | 1.7 +/− 0.3 | 65 | 0.001 |
| Controls | | | 3.5 +/− 0.1 | | |
| SR 25990E | 10 | 3.84 | 2.1 +/− 0.5 | 40 | 0.05 |
| | 20 | 7.69 | 1.4 +/− 0.4 | 60 | 0.01 |
| Controls | | | 3.97 +/− 0.29 | | |
| PCR 4099 | 2.5 | 2.14 | 3.13 +/− 0.33 | 21 | n.s |
| (racemate) | 5 | 4.28 | 2.94 +/− 0.34 | 26 | 0.05 |
| | 12.5 | 10.71 | 2.19 +/− 0.42 | 45 | 0.01 |
| SR 25989A | 25 | 22.46 | 4.32 +/− 0.29 | 10 | n.s |
| SR 25990A | 2.5 | 2.25 | 3.05 +/− 0.19 | 23 | 0.05 |
| | 5 | 4.49 | 1.24 +/− 0.22 | 69 | 0.001 |
| | 12.5 | 11.23 | 0.86 +/− 0.14 | 78 | 0.001 |
| | 25 | 22.46 | 0.74 +/− 0.13 | 81 | 0.001 |

**Student test
n.s. not significant

The antithrombotic activity of these compounds has also been studied in the test of venous thrombosis on a screw thread described by Kumada T. et al. in Thromb. Res 18 p. 189 (1980).

Female rats of the same type as those previously described, in groups of 10 animals, were anesthetized with diethyl ether and their vena cava was isolated after abdominal incision.

A metallic screw thread 21 mm long consisting of a dentist's drill, marketed by Dyna (France) size No. 30, was introduced into the lumen of this vein just below the renal bifurcation descending towards the iliac veins, without damaging the wall; 19 to 20 mm of the length of the screw thread are implanted and the remaining 1 mm protrudes through the closed stomach into the exterior.

The thrombi formed rapidly and five hours later, under pentobarbital anesthesia, the abdomen is reopened and ligatures are placed above and below the screw thread which is withdrawn after longitudinal incision of the vein and the isolated thrombus is weighed.

The results which are presented in Table III show that the levo-rotatory isomer is inactive in this test, in contrast to the dextro-rotatory isomer and the racemate.

TABLE III

| PRODUCT | DOSE mg/Kg P.O admin. | QUANTITY of base | WEIGHT of thrombi* | VARIATION % | P** |
|---|---|---|---|---|---|
| Controls | | | 3.9 +/− 0.3 | | |
| PCR 4099 | 4.48 | 3.84 | 2.17 +/− 0.24 | 44 | 0.001 |
| (racemate) | 8.97 | 7.69 | 1.39 +/− 0.15 | 64 | 0.001 |
| | 17.9 | 15.38 | 1.00 +/− 0.19 | 74 | 0.001 |
| SR 25989C | 40 | 30.76 | 4.17 +/− 0.42 | −7 | n.s |
| SR 25990C | 1.25 | 0.96 | 3.11 +/− 0.32 | 20 | n.s |
| | 2.5 | 1.92 | 2.29 +/− 0.22 | 41 | 0.01 |
| | 5 | 3.84 | 1.71 +/− 0.24 | 56 | 0.01 |
| | 10 | 7.69 | 1.26 +/− 0.19 | 67 | 0.01 |
| | 20 | 15.38 | 1.20 +/− 0.13 | 69 | 0.01 |

TABLE III-continued

| PRODUCT | DOSE mg/Kg P.O admin. | QUANTITY of base | WEIGHT of thrombi* | VARIATION % | P** |
|---|---|---|---|---|---|
| Controls | | | 3.78 +/− 0.36 | | |
| SR 25990E | 10 | 3.84 | 1.48 +/− 0.15 | 60 | 0.001 |
| | 20 | 7.69 | 1.18 +/− 0.15 | 68 | 0.001 |

* = weight of thrombi in mg +/− standard error of the mean
P = U test of Kruskal - Wallis For the toxicological study, the compounds were administered by the oral route in the form of a suspension in the same volume of water made up to 10% (wt/v) with gum arabic to groups of 10 fasted female rats of the Sprague Dawley strain weighing 120 to 135 grams.

The number of dead animals was determined 14 days after the administration of the compound under study. The lethal doses thus determined, expressed in weight of the salt administered, are presented in Table IV; these results show on the one hand that the toxicity of the racemic mixture is similar to that of the levo-rotatory isomer whereas the dextro-rotatory isomer is markedly less toxic, and, on the other hand, that the toxicity depends on the nature of the acid used to form the salt.

TABLE IV

| PRODUCTS | D 10 | D 50 ( ) | D 90 | ABSOLUTE LETHAL DOSE |
|---|---|---|---|---|
| PCR 4099 (racemate) | 1318 | 1615 (1448–1747) | 1979 | 2000 |
| SR 25989 A | 1259 | 1702 (1443–1797) | 2299 | 2000 |
| SR 25990 A | 3055 | 4316 (3569–5705) | 6137 | 5000 |
| SR 25990 C | 2257 | 2591 (2372–2805) | 2974 | 4000 |
| SR 25990 D | 2634 | 4268 (3581–6012) | 6914 | 5000 |

( ) = confidence interval

The pharmacological study just presented has demonstrated the interesting inhibitory properties towards platelet aggregation of the compound Id and the absence of any activity of its isomer I1.

The medicine of the invention can be made available for oral administration in the form of tablets, sugar-coated tablets, capsules, drops, granules or a syrup. It can also be made available for rectal administration in the form of suppositories or for parenteral administration in the form of an injectable solution.

Each unit dose contains advantageously from 0.001 g to 0.100 g of the derivative of the invention, and the daily doses to be administered may vary from 0.001 g to 0.500 g of active ingredient depending on the age of the patient and the severity of the disorder to be treated. Some pharmaceutical formulations of the medicine of the invention will be given below as non-restrictive examples.

(1) Tablets
Active ingredient: 0.010 g
Excipient: lactose, powdered sugar, rice-starch, alginic acid, magnesium stearate
(2) Sugar-coated tablets
Active ingredient: 0.005 g
Excipient: magnesium stearate, maize starch, gum arabic, shellac, white sugar, glucose, white wax, carnauba wax, paraffin, cochineal.
(3) Capsules
Active ingredient: 0.025 g
Excipient: magnesium stearate, maize starch, lactose.
(4) Injectable solution
Active ingredient: 0.050 g
Isotonic saline q.s.p. 3 ml
(5) Suppositories
Active ingredient: 0.030 g
Semi-synthetic triglycerides q.s.p. 1 suppository.

On account of its interesting inhibitory properties towards platelet aggregation and its interference in the mechanism of formation of arterial and venous thromboses, the medicine of the invention can be usefully administered in the treatment and prevention of platelet disorders due to extracoporeal blood circuits or the consequence of complications in atheroma.

We claim:

1. Dextro-rotatory isomer of methyl alpha-5(4,5,6,7-tetrahydro(3,2-c)thieno pyridyl) (2-chlorophenyl)-acetate substantially separated from the levo-rotatory isomer and its pharmaceutically acceptable salts.

2. Hydrochloride of the dextro-rotatory isomer of methyl alpha-5(4,5,6,7-tetrahydro(3,2-c)thieno pyridyl) (2-chlorophenyl)-acetate substantially separated from the levo-rotatory isomer.

3. Hydrogen sulfate of the dextro-rotatory isomer of methyl alpha-5(4,5,6,7-tetrahydro(3,2-c)thieno pyridyl) (2-chlorophenyl)-acetate substantially separated from the levo-rotatory isomer.

4. Hydrobromide of the dextro-rotatory isomer of methyl alpha-5(4,5,6,7-tetrahydro(3,2-c)thieno pyridyl) (2-chlorophenyl)-acetate substantially separated from the levo-rotatory isomer.

5. Taurocholate of the dextro-rotatory isomer of methyl alpha-5(4,5,6,7-tetrahydro(3,2-c)thieno pyridyl) (2-chlorophenyl)-acetate substantially separated from the levo-rotatory isomer.

6. Pharmaceutical composition which comprises an effective platelet aggregation inhibiting amount of a compound of claim 1 and a pharmaceutically acceptable carrier.

7. Composition according to claim 6, comprising unit doses containing from 0.001 g to 0.100 g of active ingredient.

* * * * *

US004847265C1

(12) EX PARTE REEXAMINATION CERTIFICATE (7571st)

United States Patent
Badore et al.

(10) Number: US 4,847,265 C1
(45) Certificate Issued: Jun. 29, 2010

(54) DEXTRO-ROTARORY ENANTIOMER OF METHYL ALPHA-5 (4,5,6,7-TETRAHYDRO (3,2-C) THIENO PYRIDYL) (2-CHLOROPHENYL)-ACETATE AND THE PHARMACEUTICAL COMPOSITIONS CONTAINING IT

(75) Inventors: Alain Badore, Roquettes (FR); Daniel Fréhel, Toulouse (FR)

(73) Assignee: Sanofi-Aventis, Paris (FR)

Reexamination Request:
No. 90/009,474, Jun. 1, 2009

Reexamination Certificate for:
Patent No.: 4,847,265
Issued: Jul. 11, 1989
Appl. No.: 07/155,550
Filed: Feb. 12, 1988

(30) Foreign Application Priority Data

Feb. 17, 1987 (FR) ............................................ 87 02025
Nov. 27, 1987 (FR) ............................................ 87 16516

(51) Int. Cl.
*C07J 41/00* (2006.01)
*C07D 495/00* (2006.01)
*C07D 495/04* (2006.01)

(52) U.S. Cl. ........................................ 514/301; 546/114
(58) Field of Classification Search ........................ None
See application file for complete search history.

(56) References Cited

U.S. PATENT DOCUMENTS

| | | | |
|---|---|---|---|
| 3,287,221 A | 11/1966 | Muller | |
| 3,329,570 A | 7/1967 | Allais | |
| 3,391,189 A | 7/1968 | Mull | |
| 3,796,749 A | 3/1974 | Holdrege | |
| 3,832,388 A | 8/1974 | Lorenz | |
| 4,051,141 A | 9/1977 | Castaigne | |
| 4,072,698 A | 2/1978 | Hylton et al. | |
| 4,115,439 A | 9/1978 | Aoki | |
| 4,115,568 A | 9/1978 | Chakrabarti et al. | |
| 4,242,360 A | 12/1980 | Pailer | |
| 4,258,192 A | 3/1981 | Okamoto | |
| 4,332,819 A | 6/1982 | Etschenberg | |
| 4,529,596 A | 7/1985 | Aubert et al. | |
| 5,989,578 A | 11/1999 | Bernat | |
| 6,248,729 B1 | 6/2001 | Coniglio | |
| 6,495,691 B1 | 12/2002 | Horne | |

FOREIGN PATENT DOCUMENTS

| | | |
|---|---|---|
| CA | 1194875 | 10/1985 |
| EP | 0099802 | 7/1983 |
| FR | 82 12599 | 7/1982 |
| FR | 87 02025 | 2/1987 |
| FR | 87 16516 | 11/1987 |

OTHER PUBLICATIONS

Cusack, et al. "Characteristics Of ADP Receptors," Advanced Experimental Medicine And Biology, vol. 192, 29–39 (1985). [DX 176] English.

Reist et al., "Very Slow Chiral Inversion of Clopidogrel in Rats: a Pharmacokinetic and Mechanistic Investigation," 28 Drug Metab. & Dispos. 1405. [PX 151] English.
Wilen et al., "Strategies In Optical Resolutions", 33 Tetrahedron 2725 (1977). [PX 854] English.
Jacques et al., Enantiomers, Racemates and Resolutions, Chapter 7, John Wiley and Sons, 1981. [DDX 492, DDX 492D, DDX 492E] English.
Eliel, "Racemic Modifications," Stereochemistry of Carbon Compounds, Ch. 4, pp. 31–86 (1962). [DTX 1930] English.
Vries et al., "The Family Approach to Resolution of Racemates," Angew. Chem. Int'l. Ed. 2349 (1998). [PX 852] English.
Ohm et al., "Effect of Antiplatelet Agents on Outcomes for Elderly Patients with Traumatic Intracranial Hermorrhage," 58 J. Trauma 518 ("Ohm"). [PX 182] English.
Ravin, L., et al., Chap. 75: Preformulation, Remington's Pharmaceutical Sciences, 18th ed. 1990. [PX 154] English.
Caprie Steering Committee, "Randomized Blinded Trail of Clopidogrel Versus Aspirin in Patients at Risk of Ischaemic Events," 348 The Lancet (1996). [PX 260, DDX 478] English.
Yusuf et al., "Effects of Clopidogrel in Addition to Aspirin in Patients with Acute Coronory Syndromes," 345 N. Engl. J. Med. 494 (2001). [DDX 761] English.
Ticlid Label Package Insert, with black box warning. [PX 183] English.
Betrand et al., "Double-Blind Study of the Safety of Clopidogrel ... in combination With Aspirin ..." 102 Circulation 624 (Aug. 2000). [DTX 759] English.
FDA's Policy Statement For The Development of New Stereoisomeric Drugs http://www.fda.gov/cder/guidance/stereo.htm (May 1, 1992). [PTX 188] English.
Cancer, et al., "Trends In the Development of Chiral Drugs," Drug Discovery Today 105–10 (2004). [DTX 4032] English.
Mazue, et al., Agents and Action, "Toxicological Studies of Studies of Ticlopidine in Laboratory Animals", vol. 15: 126–135 (1984). [DDX 82] English.
Panak, et al., "Ticlopidine: A Promise for the Prevention and Treatment of Thrombosis and its Complications", Haemostatsis, 13 Suppl. 1, pp. 1–54 (1983). [DDX 122] English.

(Continued)

*Primary Examiner*—Evelyn Huang

(57) ABSTRACT

The present invention relates to the dextro-rotatory enantiomer of Formula

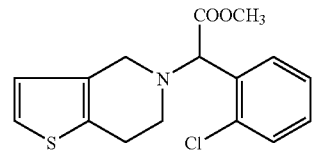

and its pharmaceutically acceptable salts with platelet aggregation inhibiting activity.
The invention also relates to a process for the preparation of this compound starting from the racemate and the pharmaceutical compositions containing it.

OTHER PUBLICATIONS

Feliste, R., et al., "Broad Spectrum anti–platelet activity of Ticlopidine and PCR 4099 ...," Thrombosis Res. 48: 403–415 (1987). [DDX 168] English.

Savi, et al., "Binding of –2–Methylthio ADP to Rat Platelets–Effect of Clopidogrel and Ticlopidine", J. Pharm. Exp. Therapeutics 269: 772–777 (1994). [DDX 169] English.

Adams, Bresloff, et al., "Pharmacological Differences Between ...", 1976, J. Pharm. Pharmac. 28, 256. [DDX 366] English.

Fasco, Principe, "R and S Warfarin Inhibition", J. Biological Chemistry, vol. 257, No. 9, 1982, 4892–4901. [DDX 367] English.

Banitt, et al., "Resolution of Flecainide", J. Med. Chem., 1986, vol. 29, No. 2, 299–302. [DDX 368] English.

Driot, Maffrand and Vallee, "Platelet–Subendothhelium Interaction: Effect of Ticlopidine," Thromp. and Haemostasis, No. 1, vol. 50, Jul. 4, 1983. [DDX 373] English.

Raiteri, et al., "Functional Evidence for Two Stereohcemically Different Alpha–2 Adrenoreceptors ...,"J. Pharm. Exp. Therap., vol. 224, No. 23, 1983. [DDX 445] English.

Klaassen and Doull, Chapter 2, "Evaluation of Safety: Toxicologic evaluation," in Casarett and Doull's Toxicology, 2d Ed. (1980). [DDX 482] English.

Mislow, Kurt. Introduction to Stereochemistry, W.A. Benjamin Inc., New York, Amsterdam, 1966. [DDX 488] English.

Jacques, et al., Enantiomers, Racemates and Resolutions, Chapter 5, "Formation and Separation of Diastereomers," (John Wiley and Sons, 1981). [DTX 489] English.

Mills et al., "Clopidogrel Inhibits the Building of ADP Analogues...," Arteriosclerosis and Thrombbosis, vol. 12., No. 4, Apr. 1992. [DDX 526] English.

Leon MB, et al., "A Clinical Trial Comparing Three Anti-thrombotic–Drug Regimens after Coronary–Artery Stenting," NEJM 339, 1665 (1998). [DDX 773] English.

Harris, G., "Study Raises Questions on Plavix Safety," New York Times, Jan. 20, 2005. [DDX 852] English.

The Merck Index (11th ed. 1989), excerpts. [PTX 1062] English.

Albert, A., "Selective Toxicity," 5th ed., p. 25, Chapman and Hall, London (1973). [DDX 1134, DDX 1134E] English.

Colman, et al., "Identification of Two Distinct Adenosine Diphosphate Receptors in Human Platelets," Trans. Am. Ass. Phys. 93:305–310 (1980). [DDX 1304] English.

Goldstein, et al., Principles of Drug Action: The Basis of Pharmacology, Second Edition, 1974 (NY, John Wiley & Sons). [DDX 1305, 1305A] English.

Newman, Optical resolution Procedures for Chemical Compounds, vol. 1, Manhattan College, Riversdale, NY (1978). [DDX 1319] English.

Boucher, M., et al., "A Critical Appraisal of the CURE Trial," The Canadian J. of Clin. Pharm., vol. 11(1): 156–67, (2004). [DDX 1616] English.

Lange, Richard A., et al., "Antiplatelet Theraphy for Ischemic Heart Disease," New England Journal of Medicine, 350(3): 277–80, 2004. [DDX 1627] English.

Schleinitz, M.D., et al. "Clopidogrel Versus Aspirin for Secondary Prohylaxis of Vascular Events," Am. J. Med., 116(12): 797–806, 2004. [DDx 1638] English.

Schornig, A., et al., "A Randomized Comparison of Antiplatelet and Anticoagulant Therapy," NEJM, 334: 1084–89, 1996. [DDX 1639] English.

Sybertz, "Alpha and Beta Andrenoceptor Blocking Properties of Labetalol" J. Pharmacognomy and Exp. Thers. 218 (2), 435 (1981). 138. [DDX 1929, 1929B, PTX 320] English.

Commit Coll. Grp., "Addition of Clopidogrel to Aspirin," The Lancet, vol. 366, Issue 9797, Nov. 2005, pp. 1–50. [DDX 2601] English.

Bhatt, et al., "Clopidogrel and Aspirin versus Aspirin Alone for the Prevention of atherothrombotic Events," NEJM (2006) 354. [DDX 2602] English.

Pfeffer, et al., "The Charisma of Subgroups and the Subgroups of CHARISMA," New England Journal of Medicine (2006), 1744. [DDX 2603] English.

Patrono, et al., "Low–Dose Aspirin for the Prevention of Atherothrombosis," New England Journal of Medicine, 353, 2373 (2005). [DDX 2615] English.

Technical desription: Plavix (clopidogrel bisulfate tablets). [DDX 704] England.

Orange Book Listing—Approved Drug Products re: 4'529'596 Patent, 19th Edition, 1999. [DDX 1998] English.

Translation of Article L611–7 of Industrial Property. [DDX 4033] English (Translation).

Thébault, J., McEwen, J., McGraw, A., Bouloux, C., Jacob, C., Chigot, C., Irvine, A., Kindermans, M., Maffrand, J.P., Roncucci, R., "PCR 4099, A New Anti–thrombotic Drug. Evaluation of Tolerance and Pharmacological Activity," Thrombosis Research, Suppl. VI at 144 (No. 286) (1986).

Thébault, J.,Bouloux, C., McEwen, J., McGraw, A., Jacob, C., Irvine, A., Kindermans, M., Maffrand, J.P., Roncucci, R., "PCR 4099, A New Anti–thrombotic Drug. Evaluation of Tolerance and Pharmacological Activity," (S 64731A).

R.W. Colman and W.R. Figures, "Characteristics of an ADP receptor mediating platelet activation," Molecular and Cellular Biochemistry 59:101–111 (1984).

E.J. Ariens, "Stereochemistry, a Basis for Sophisticated Nonsense in Pharmacokinetics and Clinical Pharmacology," Eur. J. Clin. Pharmacol. 26:663–668 (1984).

Williams and Lee, "Importance of Drug Enantiomers in Clinical Pharmacology," Drugs 30:333–354 (1985).

"Pharmaceutical Manufacturing Guidelines," 1985 Edition (with translation), edited by The Society of the Japanese Pharmacopoeia and published Oct. 22, 1985 by Yakugyo Jiho–Saa (The Pharmaceutical Times Company).

The Center for Drug Evaluation and Research of the Food and Drug Administration distributed "Guideline for Submitting Supporting Documentation in Drug Applications for the Manufacture of Drug Substances," Dated Feb. 1987.

Goldstein, Aranow and Kaplan, Principles of Drug Action: The Basis of Pharmacology, 2D ED. (New York, John Wiley & Sons 1974).

W. Soudjin, "Advantages and Disadvantages in the Application of Bioreactive Racemates or Specific Isomers as Drugs," in Stereochemistry and Biological Activity of Drugs (London, Blackwell Scientific Publications 1983). pp. 89–102.

Karrer, P., Organic Chemistry, Second Ed. (New York: Elsevier Publ. Co. 1946).

Graham, D.G., "Catechlolamine Toxicity: A Proposal for the Molecular Pathogenesis of Manganese Neurotoxicity and Parkinson's Disease," Neurotoxicology 5: 83–96 (1984).

Cotzias, G.C., et al., "Modification of Parkinson—Chronic Treatment With L–Dopa," New Eng. J. Of Medicine 280:337–345 (1969).

Gould, P.L., "Salt selection for basic drugs," International Journal for Pharmaceutical 33:201–217 (1986).

Berge, S.M., Bighley, L.D., and Monkhouse, D.C., "Pharmaceutical Salts," Journal of Pharmaceutical Sciences 66:1–19 (1977).

Feiser and Feiser, Advanced Organic Chemistry (Reingold Publ. Co. 1961), pp. 85–88.

Di Minno G, et al. Cerbone AM, Mattioli PL, Turco S, Iovine C, Mancini M. Functionally thrombasthenic state in normal platelets following the administration of ticlopidine, J. Clin Invest. 1985 Feb;75(2)328–38.

Lehmann, P.A., Rodrigues de Miranda, and Ariens, E.J., "Stereoselectivity and Affinity in Molecular Pharmacology," in Jucker (ed.), Progress in Drug Research, 20, 1–77 (1976).

Center for Drug Evaluation and Research List of Guidance Documents.

Maffrand, J.P., Vallée, E., Bernet, A., Delebassé, D., Millou, E., Tissinier, A., Ronocucci, R., "Animal Pharmacology of PCR 4099, a New Thienopyridine Compound," Thrombosis and Heamostasis 54:133 (P789) (Jul. 14, 1985).

Maffrand, J.P., Vallée, E., Bernat, A., Delebassé, D., Millou, E., Tissinier, A., Ronocucci, R., "Animal Pharmacology of PCR 4099, a New Thiernopyridine Compound," S 277247.

Delebassé, D., Vallée, E., Chap, H., Simon, M.F., Roncucci, R., and Maffrand, J.P., "Effect of Ticlopidine and PCR 4099 on Cellular Signal Transduction in Rat Platelets," Thrombosis and Haemostasis 54; 132 (P784) (Jul. 14, 1985).

Delebassé, D., Vallée, E., Roncucci, R., and Maffrand, J.P., Felisté, R., Chap, H., Simon, M.F., and Douste–Blazy, L., "Effect of Ticlopidine and PCR 4099 on Cellular Signal Transduction in Rat Platelets," S 277148.

Thébault, J., Blatrix, C., Bouloux, C., Chigot, C., Armagnac, C., Maffrand, J.P., Vallée, E., Roncucci, R., "PCR 4099. A New Thienopyridine Derivative with Potent Antiplatelet Activity in Man," Thrombosis and Haemostasis 54:177 (P1049) (Jul. 14, 1985).

Thébault, J., Blatrix, C., Armagnac, C., Bouloux, C., Chigot, C., Maffrand, J.P., Vallée, E., Roncucci, R., "PCR 4099. A New Thienopyridine Derivative with Potent Antiplatelet Activity in Man," S 272968.

Delebassé, D., Vallée, E., Beretz, A., Gachet, C., Cazenave, J.P. Maffrand, J.P., "Platelet Aggregation in Fawn Hooded Rats: Evidence that PCR 4099 Inhibits Selectivity the Platelet ADP Pathway," Thrombosis Research, Suppl. VI at 146 (No. 290) (1986).

Delebassé, D., Vallée, E., Beretz, A., Gachet, C., Cazenave, J.P. Maffrand, J.P., "Platelet Aggregation in Fawn Hooded Rats: Evidence That PCR 4099 Inhibits Selectivity the Platelet ADP Pathway," (S 277149).

Decision of the Federal Court of Australia, New South Wales District Registry; NSD 1311 of 2008; dated Sep. 29, 2009.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-7 is confirmed.

* * * * *